United States Patent
Beau et al.

(10) Patent No.: US 9,888,681 B2
(45) Date of Patent: *Feb. 13, 2018

(54) ASSEMBLY FOR FREEZING A PLURALITY OF CONDITIONING TUBES EACH FILLED WITH A PREDETERMINED VOLUME OF BIOLOGICAL SUBSTANCE

(71) Applicant: IMV TECHNOLOGIES, Saint Ouen sur Iton (FR)

(72) Inventors: Christian Beau, Voisin le Bretonneux (FR); Agnes Camus, Sainte Gauburge Sainte Colombe (FR); Eric Schmitt, Villaines-la-Juhel (FR)

(73) Assignee: IMV TECHNOLOGIES, Saint Ouen sur Iton (FR)

( * ) Notice: Subject to any disclaimer, the term of this patent is extended or adjusted under 35 U.S.C. 154(b) by 476 days.

This patent is subject to a terminal disclaimer.

(21) Appl. No.: 13/623,661

(22) Filed: Sep. 20, 2012

(65) Prior Publication Data

US 2013/0067950 A1    Mar. 21, 2013

(30) Foreign Application Priority Data

Sep. 20, 2011    (FR) .................................... 1158329

(51) Int. Cl.
*F25D 11/00* (2006.01)
*A01N 1/02* (2006.01)
(Continued)

(52) U.S. Cl.
CPC ......... *A01N 1/0252* (2013.01); *A01N 1/0284* (2013.01); *F25D 3/11* (2013.01); *F25D 17/06* (2013.01)

(58) Field of Classification Search
CPC . F25D 3/11; F25D 3/105; F25D 70/06; F25D 17/06; A01N 1/0242; A01N 1/0252
(Continued)

(56) References Cited

U.S. PATENT DOCUMENTS 1,429,435 A * 9/1922 Jones .................... F25D 17/005
165/108
2,441,730 A * 5/1948 Strumia .................... A23L 3/44
165/111
(Continued)

FOREIGN PATENT DOCUMENTS

EP    0353592 A2 *    2/1990    .............. B01L 3/508
EP    0353592 A2 *    7/1990    .............. G01N 35/02
(Continued)

*Primary Examiner* — Ljiljana Ciric
*Assistant Examiner* — Kirstin Oswald
(74) *Attorney, Agent, or Firm* — Browdy and Neimark, P.L.L.C.

(57) ABSTRACT

An assembly is provided for freezing a plurality of conditioning tubes each filled with a predetermined volume of biological substance, in which each of the tubes is driven in rotation in a flow of cooling agent, the assembly including a cooling enclosure configured in order to be passed through by the flow of cooling agent and a conditioning unit which is removable and placed in the enclosure; the unit is provided with a greater capacity than the plurality of tubes in order to directly receive this plurality of the tubes, the enclosure is fixed and the assembly includes a unit for driving the conditioning unit in rotation, which unit for driving in rotation is provided with a connection interface on which the removable conditioning unit is placed.

16 Claims, 11 Drawing Sheets

(51) Int. Cl.
*F25D 3/11* (2006.01)
*F25D 17/06* (2006.01)

(58) Field of Classification Search
USPC .............................. 62/62, 63, 345–346, 381
See application file for complete search history.

(56) References Cited

U.S. PATENT DOCUMENTS

| | | | | |
|---|---|---|---|---|
| 2,695,729 | A * | 11/1954 | Hornish | A61K 35/52 221/150 R |
| 3,172,546 | A * | 3/1965 | Schreiner | C12M 45/02 241/176 |
| 4,227,381 | A | 10/1980 | Sullivan | |
| 4,340,263 | A * | 7/1982 | Webb | B65G 1/127 312/134 |
| 5,147,042 | A * | 9/1992 | Levy | A61B 10/0096 206/453 |
| 5,176,202 | A * | 1/1993 | Richard | F25D 3/11 165/48.1 |
| 5,205,128 | A * | 4/1993 | Richard | A01N 1/02 62/441 |
| 5,233,844 | A * | 8/1993 | Knippscheer | F25D 3/102 414/331.05 |
| 5,567,050 | A * | 10/1996 | Zlobinsky | B01F 11/0008 366/110 |
| 5,921,102 | A * | 7/1999 | Vago | F25D 25/00 62/266 |
| 6,669,432 | B2 * | 12/2003 | Hamel | G01N 35/10 414/222.01 |
| 6,692,695 | B1 * | 2/2004 | Bronshtein | A61K 9/122 422/1 |
| 7,527,764 | B2 * | 5/2009 | Angelantoni | F25D 25/00 221/210 |
| 2004/0103672 | A1 * | 6/2004 | Newman | A23L 3/375 62/63 |
| 2004/0171102 | A1 * | 9/2004 | Plank | G01N 1/312 435/40.5 |
| 2004/0265173 | A1 * | 12/2004 | Matsumoto | G01N 35/025 422/64 |
| 2005/0276726 | A1 * | 12/2005 | McGill | G01N 29/036 422/96 |
| 2005/0276728 | A1 * | 12/2005 | Muller-Cohn | A01N 1/00 422/400 |
| 2006/0236703 | A1 * | 10/2006 | Rada | A01N 1/02 62/62 |
| 2009/0288429 | A1 * | 11/2009 | Elsom | A23G 9/28 62/68 |
| 2014/0075968 | A1 | 3/2014 | Beau et al. | |

FOREIGN PATENT DOCUMENTS

| | | |
|---|---|---|
| EP | 0617248 A1 | 9/1994 |
| JP | 6001142 B | 1/1994 |
| WO | 2005108885 A1 | 11/2005 |

* cited by examiner

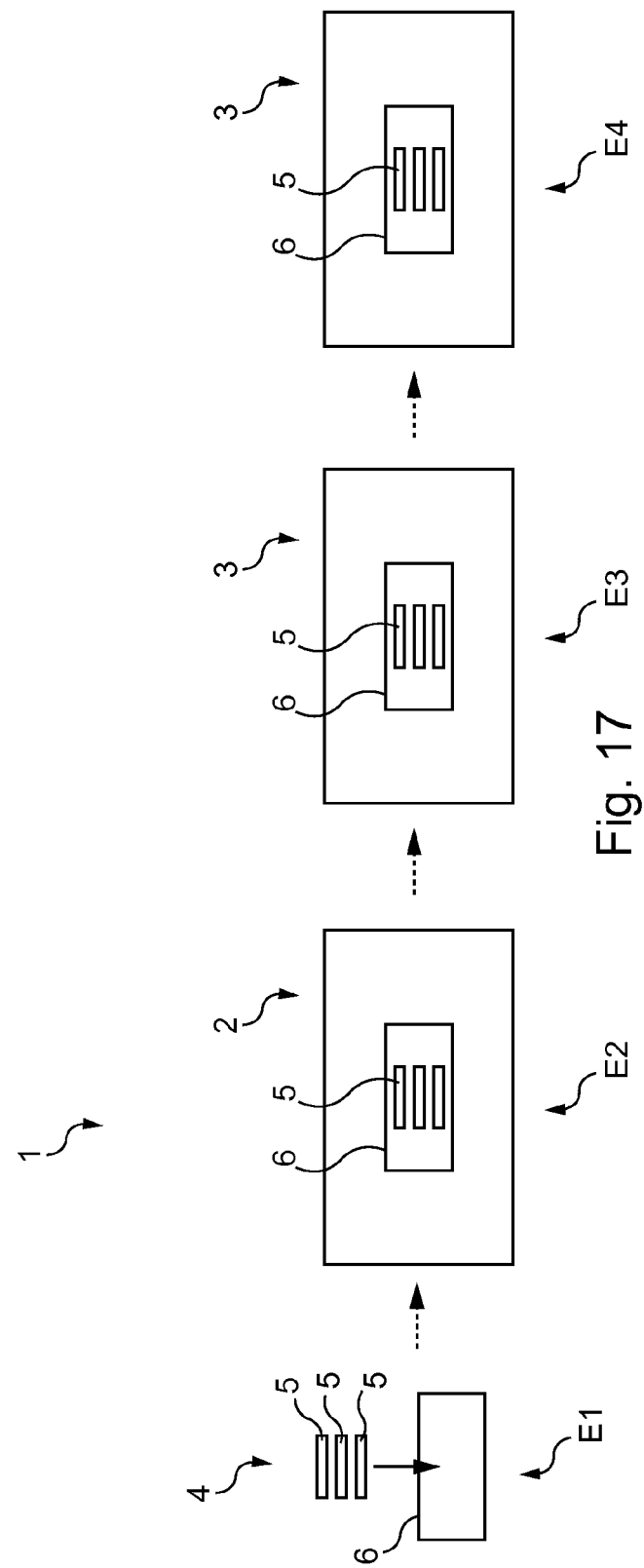

ASSEMBLY FOR FREEZING A PLURALITY OF CONDITIONING TUBES EACH FILLED WITH A PREDETERMINED VOLUME OF BIOLOGICAL SUBSTANCE

FIELD

The present invention relates to the general field of the freezing of biological substances, in particular to assemblies for freezing a plurality of conditioning tubes each filled with a predetermined volume of biological substance.

These conditioning tubes are for example capillary tubes also called "French straws".

BACKGROUND

It is known that the freezing of such French straws requires following a freezing process defining a temperature kinetics in order to cool the biological substance to a negative temperature below its glass transition zone.

This temperature kinetics is made possible by the implementation of a first phase called equilibration phase and a second phase called freezing phase, which can be divided into several freezing sub-phases.

For example, the French straws are arranged at a temperature of the order of +4° C. for a first specific period, for example a few hours, for resting. This is the equilibration phase. Then, the French straws are subjected to a first drop in temperature, firstly from +4° C. to −10° C. in steps of the order of −5° C./min; then a second drop in temperature from −10° C. to −140° C. in steps of the order of −40° C./min. These are respectively the first and second freezing sub-phases comprised by the freezing phase.

The kinetics disclosed above is specified in the case where the filling phase is carried out at ambient temperature.

It will be observed that the temperature kinetics depends on the phase of filling the French straws since in fact, the implementation of this kinetics differs depending on whether this filling phase is carried out at ambient temperature or at a temperature below ambient temperature.

In the case where the French straws are filled at a temperature of the order of +4° C., the equilibration phase is then not necessary and the French straws are directly introduced into a freezing system.

In order to achieve such kinetics, it is necessary to have a filling system and a freezing assembly comprising in particular several freezing systems (or a freezing system provided with several cold zones) and optionally an equilibration system.

Generally, in order to be filled, the French straws are arranged horizontally and in ordered manner, i.e. arranged flat, in specific grooves arranged on a mobile conveyor. These grooves are shaped so that they can receive a particular type of French straws in order that the latter are arranged homogeneously.

After the French straws have each been filled with a certain volume of biological substance at ambient temperature, they are extracted from the grooves on the conveyor of the filling machine and are introduced into plastic boxes, which are themselves also shaped so that the French straws are aligned side by side each other, i.e. arranged homogeneously. These boxes are placed in an equilibration zone to rest. Then, the French straws are extracted from the plastic box to be introduced into freezing systems.

In the case where the French straws are each filled with a predetermined volume of biological substance at a temperature of the order of +4° C., they are then extracted from the grooves on the conveyor of the filling machine and are directly introduced into freezing systems.

These freezing systems are generally in the form of a conventional freezer in which racks are arranged horizontally, which are provided with locations intended to receive in an ordered manner French straws each previously filled with a certain volume of biological substance. As a variant, each French straw is introduced into a specific cylindrical or hexagonal tube, some (a predetermined number) of these cylindrical or hexagonal tubes are introduced into and arranged in a beaker and several beakers are arranged vertically and stacked inside a canister that is itself arranged vertically in the freezer.

From the American patent U.S. Pat. No. 4,227,381 a system of freezing is also known, in particular of French straws filled with biological substance, provided with a cooling enclosure passed through by a flow of cooling agent entering this chamber by an inlet duct and leaving this enclosure by an outlet duct. This enclosure has an internal space into which is introduced a single container having a plurality of conditioning cases arranged in an ordered manner, i.e. aligned side by side and stacked, inside the container. In each conditioning case is arranged a French straw or an ampule previously filled with a volume of biological substance to be frozen.

The container, the cases introduced into this container as well as the French straws or ampules each filled with a volume of biological substance and introduced into these cases are arranged in the cooling enclosure in a direction similar to that defined between its inlet connector and its outlet connector.

The system is moreover provided with a unit for driving the cooling enclosure in rotation on itself. For this, the cooling enclosure is in mechanical inter-engagement allowing the driving in rotation at the level of its inlet connector. This cooling enclosure is also in mechanical inter-engagement allowing the rotation at the level of its outlet connector, which outlet connector is connected to an outlet duct for the flow of cooling agent.

In order to freeze the French straws, the cooling enclosure is set in rotation on itself and the flow of cooling agent flows along the closed container which comprises the cases each containing a French straw. The French straws are therefore driven in rotation whilst being held in the cases, which are held in the single container.

SUMMARY

The invention relates to an assembly aimed at simplifying the freezing process implemented in the freezing assemblies of the state of the art in a simple, convenient and economical manner.

A subject of the invention is thus an assembly for freezing a plurality of conditioning tubes each filled with a predetermined volume of biological substance, in which each said conditioning tube is driven in rotation in a flow of cooling agent, said assembly comprising a cooling enclosure configured in order to be passed through by said flow of cooling agent and a conditioning unit which is removable and placed in said cooling enclosure; said assembly being characterized in that said conditioning unit is provided with a greater capacity than said plurality of said conditioning tubes in order to directly receive this plurality of said conditioning tubes; in that said cooling enclosure is fixed; and in that it comprises a unit for driving said conditioning unit in rotation, which unit for driving in rotation is provided with a connection interface on which said removable conditioning unit is placed.

In the assembly according to the invention, the cooling enclosure is fixed and therefore the conditioning unit is driven in rotation with respect to this enclosure in which it is placed. The conditioning tubes are therefore also driven in rotation with respect to the enclosure.

The direct arrangement of a plurality of conditioning tubes in the same conditioning unit, which is therefore the primary container of the tubes as well as each individual case of the abovementioned previous system, the removable character of the conditioning unit, its configuration for being set in rotation and the fact that the latter can be easily placed on the connection interface of the unit for driving in rotation, makes it possible for this conditioning unit to be used during all of the freezing process, i.e. during the equilibration phase if there is one, as well as during the freezing phase.

This means that after the filling of the conditioning tubes, the latter can be introduced directly into the conditioning unit, which can then be arranged in an equilibration zone for a predetermined period; then this conditioning unit can be extracted from this equilibration zone in order to be introduced into a cold zone for the freezing phase. As a variant, after the filling of the conditioning tubes (at a predetermined temperature below ambient temperature), these tubes are introduced into the conditioning unit, which is directly arranged in a cold zone for the freezing phase.

It will of course be observed that if the freezing phase has several sub-phases which take place in different cold zones, the conditioning unit can be moved from one of these zones to another without additional handling of the conditioning tubes.

Thanks to the invention, a single operation of placing the conditioning tubes in the conditioning unit is sufficient after the filling of these conditioning tubes, which simplifies the entire freezing process since a certain number of handling operations of the conditioning tubes can thus be avoided.

It will be observed that in the known systems, the ordered arrangement of the conditioning tubes (in other words a certain homogeneity of arrangement) is considered as a step indispensable to the homogeneity of freezing of these tubes.

The work carried out by the inventors has in fact revealed that, surprisingly, the stirring of the conditioning tubes in the conditioning unit not only does not prevent the homogeneity of freezing but, on the contrary, promotes this homogeneity.

It will also be observed that in the method according to the invention, the conditioning tubes can be placed loose inside the conditioning unit.

The assembly according to the invention therefore makes it possible to simplify the process of freezing the tubes each filled with a volume of biological substance whilst remaining particularly convenient and economical.

According to preferred, simple, convenient and economical characteristics of the assembly according to the invention:
- it comprises an equilibration system provided with an equilibration zone at a first predetermined stable temperature, which zone is configured in order to receive said at least one conditioning unit during a first predetermined period;
- it comprises at least one freezing system provided with at least one freezing zone formed by said cooling enclosure, which zone is configured in order to be cooled down by said flow of cooling agent which circulates there, between a second predetermined temperature and a third predetermined temperature;
- said second predetermined temperature is below or equal to said third predetermined temperature;
- said unit for driving in rotation is mounted on said cooling enclosure;
- said unit for driving in rotation is fixed to the outside of said cooling enclosure and has a drive shaft extending from said unit for driving in rotation and continuing until it opens inside said cooling enclosure, said drive shaft being provided at one end of said connection interface, which end is situated in said cooling enclosure;
- said connection interface is formed by a support provided with a fixing part configured in order to cooperate with said conditioning unit;
- said conditioning unit has a metallic back wall and the fixing part is formed by a magnetic portion arranged in said support, which magnetic portion allows the fixing of said conditioning unit to said support by magnetism, using said back wall;
- said conditioning unit is configured in order to be driven in rotation on itself;
- said conditioning unit has at least one longitudinal side wall and an internal space configured in order to receive, in said longitudinal direction of said at least one side wall, said plurality of said conditioning tubes; and/or
- said conditioning unit is configured in order to be placed in said cooling enclosure so that said flow of cooling agent meets said at least one side wall.

According to other preferred simple, convenient and economical characteristics of the assembly according to the invention, said conditioning unit has at least one longitudinal side wall in which at least one opening is arranged and said at least one conditioning unit is arranged in said enclosure so that said flow of cooling agent passes through said at least one opening in order to meet said conditioning tubes.

The opening arranged in the conditioning unit makes it possible to subject the conditioning tubes (introduced into the unit) to both a thermal convection phenomenon and a thermal conduction phenomenon for freezing the volumes of biological substance present in these tubes. In fact, the conduction phenomenon is produced when the conditioning tubes come into contact with an internal side surface of the side wall of the conditioning unit due to the fact that the flow of cooling agent also comes into contact with this side wall (on an external side surface); and the convection phenomenon is produced when this flow of cooling agent passes through the opening and comes directly into contact with the conditioning tubes.

According to other preferred simple, convenient and economical characteristics of the assembly according to the invention:
- said at least one opening is in the form of a window extending in said longitudinal direction;
- said at least one opening is formed by a series of through slots arranged successively in said longitudinal direction, each slot having a main direction distinct from said longitudinal direction;
- said conditioning unit has at least one longitudinal side wall and comprises a metallic removable cover; and at least one magnetic component allowing said removable cover to be fixed to said at least one side wall by magnetism;
- said cover has a gripping portion;
- it comprises several conditioning units each provided with a front wall and a back wall opposite said front wall, which, with said at least one side wall, at least partially define an internal space; a first of said conditioning units has a receiving orifice arranged in said front wall and configured in order to receive a connecting element projecting from a back wall of a second of said conditioning units with which said first conditioning unit is arranged to cooperate; and said first conditioning unit has a connecting element projecting from said back wall and configured in order to be introduced into a receiving orifice arranged in a front wall of a third of said conditioning units with which said first conditioning unit is also arranged to cooperate; and/or said conditioning unit has a front wall and a back wall opposite said front wall, which, with at least one side wall, at least partially define an internal space; said front wall is configured in order to be mounted flush with a first end of said at least one side wall; and said back wall is configured in order to be mounted against said internal side surface of said at least one side wall, close to a second end of this side wall which is opposite said first end.

BRIEF DESCRIPTION OF THE DRAWINGS

The disclosure of the invention will now continue with a description of embodiment examples, given below for the purposes of illustration and non-limitatively, with reference to the attached drawings in which:

FIG. 17 represents diagrammatically an assembly for freezing a plurality of conditioning tubes each filled with a volume of biological substance.

DETAILED DESCRIPTION

Figure 1:
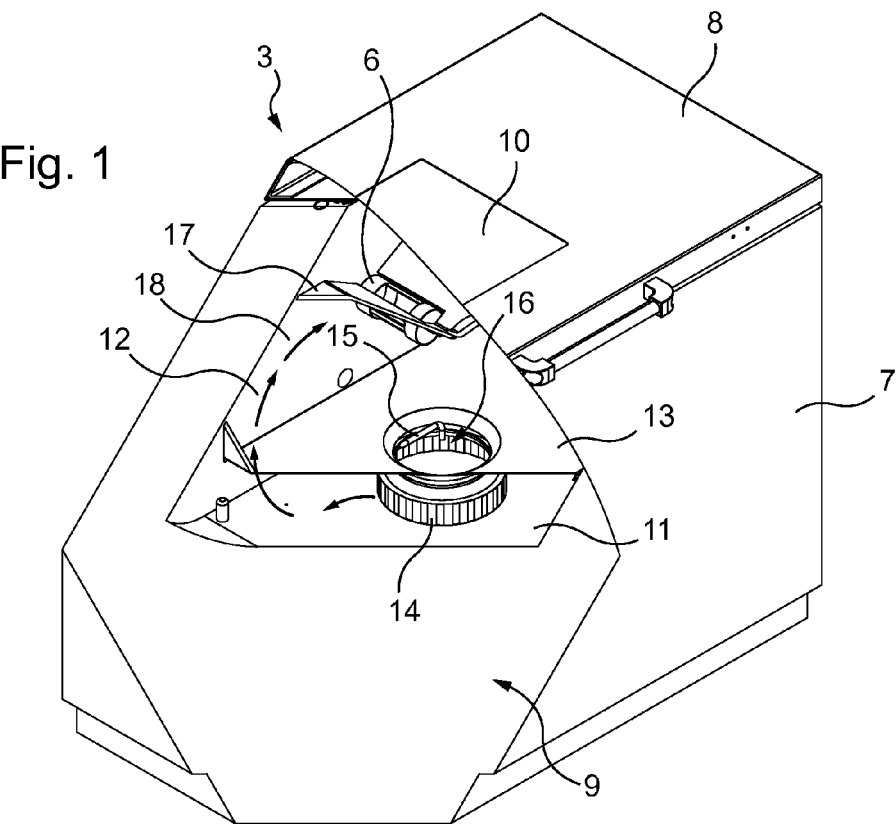
FIG. 1 represents, diagrammatically in perspective, a freezing system according to a first embodiment, which system is partially cut away in order to show its interior and in particular a conditioning unit which is arranged there.

With reference to FIGS. 1 to 3 and 11, two freezing systems 3 and 203 are shown, configured in order to freeze conditioning tubes 5 each filled with a predetermined small volume of biological substance.

The concept of freezing is meant here in the general sense of the word and therefore means a drop in temperature to a negative temperature, below 0° C.

The biological substance to be frozen is here formed for example by seminal fluid or also by tissue samples. This biological substance requires cooling to a negative temperature below its glass transition zone in order to allow handling with the minimum of risk to the biological cells that it comprises.

The concept of freezing thus covers in this case temperatures which can go down to −140° C., or even temperatures below −150° C.

The freezing of this biological substance requires following temperature kinetics in order to bring it down to a negative temperature below its glass transition zone.

This temperature kinetics is made possible by the implementation of a first phase called equilibration phase and a second phase called freezing phase, which can be divided into several freezing sub-phases.

For example, after filling the conditioning tubes at ambient temperature, these tubes are arranged at a temperature of the order of +4° C. for a first specific period, for example a few hours, for resting. This is the equilibration phase. Then, these tubes are subjected to a first drop in temperature, firstly from +4° C. to −10° C. in steps of the order of −5° C./min; then a second drop in temperature from −10° C. to −140° C. in steps of the order of −40° C./min. These are respectively the first and second freezing sub-phases comprised by the freezing phase.

In order to achieve such kinetics, it is necessary to have a freezing assembly 1 comprising an equilibration system 2 and several freezing systems 3. Such an assembly can be seen in FIG. 17.

FIG. 17 illustrates the freezing process as defined above.

Of course, previous and subsequent steps are necessary.

Firstly, the conditioning tubes, called here French straws 5, are each filled with a predetermined volume of biological substance in specific filling machines (filling step not shown), here at ambient temperature, i.e. approximately 20° C. In order to carry out this filling step, the French straws are generally arranged flat on a conveyor.

Following this step of filling the French straws 5, the freezing process as defined above can start with a step of introduction of a certain number of French straws 5 into a conditioning unit 6 forming a receptacle called a drum in the remainder of the description. This step, also called the drum 6 filling phase, is denoted E1 in FIG. 17 and is carried out at a drum 6 filling station 4.

The French straws 5 are placed loose in the conditioning unit 6. In other words, no ordered arrangement of the French straws 5 is sought at this stage.

Moreover, it will be observed that a plurality of French straws 5 is introduced into the unit 6, for example between approximately 50 and approximately 200 French straws, which represents a filling volume of the drum 6 of approximately 10% to approximately 30% of its capacity.

Its capacity is therefore greater than the plurality of French straws.

The freezing process continues with an equilibration step E2, also called an equilibration phase or also a first phase, carried out in an equilibration system 2.

This equilibration system 2 comprises a refrigerated display case (not shown) into which the drum 6 containing the French straws 5 is introduced.

As indicated above, the refrigerated display case is at a first predetermined temperature, for example of the order of +4° C. The drum 6 is arranged in this refrigerated display case for a first predetermined period, for example a few hours.

The freezing process continues with the extraction of the drum 6 from the equilibration system 2 and the arrangement of this drum 6 in a first freezing system 3 for a first freezing step E3, also called a first freezing sub-phase.

This first freezing system 3 is also at a second predetermined temperature, for example also of the order of +4° C. and this first freezing system 3 is moreover configured in order to lower this second predetermined temperature to for example −10° C. using a flow of cooling agent such as gaseous nitrogen in steps of approximately −5° C./min.

The freezing process again continues with the extraction of the drum 6 from the first freezing system 3 followed by the insertion of this drum 6 into a second freezing system 3 (similar to the first freezing system 3) for a second freezing step E4, also called a second freezing sub-phase.

This drum 6 is arranged in this second freezing system 3 at a third predetermined temperature, for example of the order of −10° C.

This second freezing system 3 is configured in order to lower this third predetermined temperature until it reaches for example −140° C., or even −150° C. thanks to the circulation of a flow of cooling agent such as gaseous nitrogen, in steps of approximately −40° C./min.

The freezing process as defined above is completed at the end of step E4.

During steps E1 to E4, the French straws 5 only need to be handled once, since it is then the drum 6 which is handled with the French straws 5 inside.

A subsequent storage step is generally implemented. This storage step requires the extraction of the drum 6 from the second freezing system 3 and the placing of the drum 6 directly into a storage system (not shown) for example formed by a tank filled with a cooling agent such as liquid nitrogen which will directly receive the drum 6. As a variant, the French straws 5 are extracted from the drum 6 and immersed directly in this tank of liquid nitrogen; or the French straws 5 are extracted from the drum 6 and introduced in a larger quantity into a specific beaker, which is immersed in the tank of liquid nitrogen.

Figure 2:
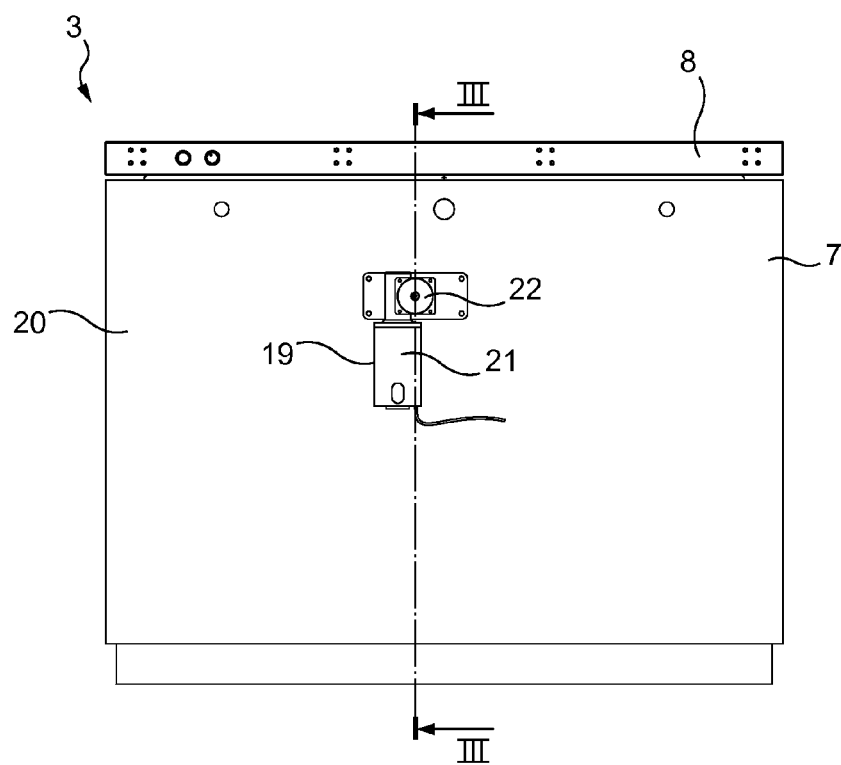
FIG. 2 is a rear view of the system of FIG. 1.
Figure 3:
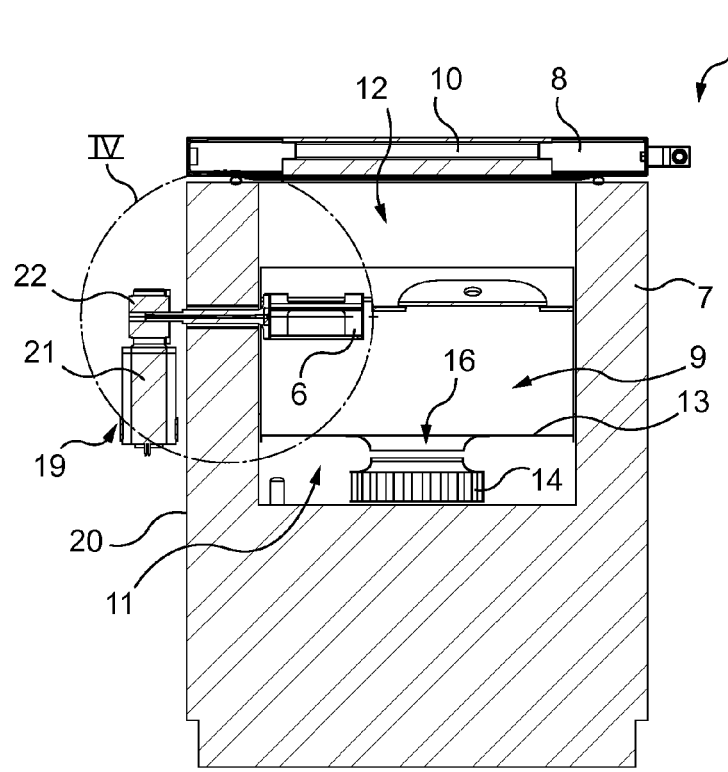
FIG. 3 is a cross-sectional view along III-III in FIG. 2.

FIGS. 1 to 3 illustrate a freezing system 3.

This freezing system 3 has a rectangular parallelepipedic shape similar to that of a conventional freezer.

This freezing system 3 has a box 7 surmounted by a cover 8 hinged to this box 7.

This box 7 has an internal space forming a cooling enclosure 9. The cover 8 has a glazed opening 10 making it possible to see inside this enclosure 9.

The cooling enclosure 9 forms a cold chamber divided into a lower zone 11 and an upper zone 12.

The lower zone 11 is a zone for the arrival and expulsion of a cooling agent such as nitrogen passing from its liquid form to its gaseous form.

The freezing system 3 also has a partial separation plate 13 forming an interface between the upper zone 12 and the lower zone 11 as well as an expulsion device 14, such as a turbine provided with blades, arranged under the plate 13 in the lower zone 11.

The separation plate 13 is provided with a circular orifice 16 passing through it, which opens into the centre of the turbine 14.

The freezing system 3 also has a duct 15 for conveying nitrogen in liquid form which opens into the centre of the orifice 16.

This duct 15 forms part of an injection device provided in particular with a solenoid valve (not shown), which is configured in order to deliver nitrogen present in a specific reservoir and control the flow rate of liquid nitrogen injected into the cooling enclosure 9.

FIG. 1 also shows that the drum 6 into which French straws 5 (not visible) are inserted is introduced into the upper zone 12 of the freezing system 3.

The freezing system 3 also has a guide plate 17 fixed against an internal wall 18 in the upper zone 12.

This guide plate 17 is arranged close to the drum 6 and has specific shapes configured in order to guide the flow of cooling agent, as described below.

The freezing system 3 also has a unit for driving in rotation 19 formed here by an electric motor 21 associated with a reduction gear 22.

Figure 4:
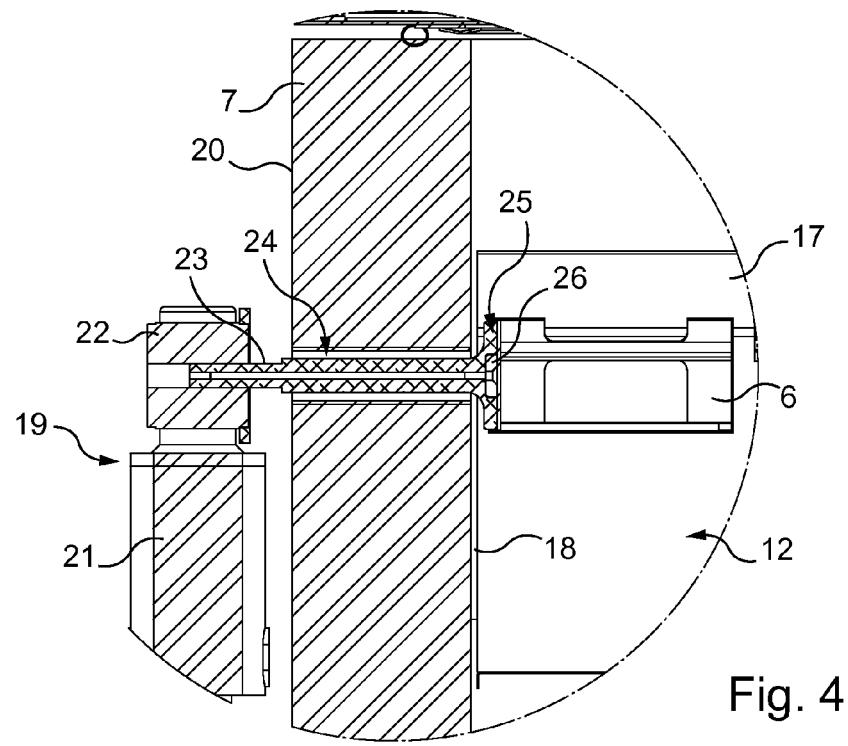
FIG. 4 is a detailed view along IV-IV in FIG. 3.

This unit for driving in rotation 19 is fixed to a rear face 20 of the box 7, i.e. outside the cooling enclosure 9 (FIGS. 2 to 4).

This unit for driving in rotation 19 is moreover provided with a rotating shaft 23 which extends from the reduction gear 22, which passes through an orifice 24 arranged in the rear face 20 of the box 7, with this orifice 24 opening into the upper zone 12.

This rotating shaft 23 has one end opposite the reduction gear 22 which end is arranged in the upper zone 12 and is provided with a support 25 formed here by a shoulder formed on this shaft 23.

This support 25 has a magnetic portion 26 in its centre.

The support assembly 25 and its magnetic portion 26 form a connection interface with the drum 6.

Of course, this freezing system 3 is configured so that the upper zone 12 is at least partially impervious to the gaseous fluids despite the orifice 24.

FIGS. 3 and 4 show that the drum 6 is fixed directly to the connection interface formed by the support 25 and its portion 26.

Thus, this drum 6 is configured in order to be driven in rotation by the rotating shaft 23 of the unit for driving in rotation 19.

The drum 6 is in this case made of metal, removable and fixed in a non-permanent manner to the support 25 by magnetism using the magnetic portion 26.

The drum 6 will now be described in more detail with reference to FIGS. 5 to 7.

The drum 6 is generally circular, or even cylindrical in shape.

This drum 6 is provided with a cylindrical side wall 27, a front wall 28 and a back wall 29; which walls 27, 28 and 29 define an internal space 30 of the drum 6, representing its capacity.

The cylindrical side wall 27 extends in a general longitudinal direction.

The side wall 27 in this case has a first end 31 and a second end 32 opposite the first end 31.

The drum 6 also has three openings each in the form of a window 33 arranged in the side wall 27.

These windows 33 extend both longitudinally and over the contour of this side wall 27.

These three windows 33 are regularly spaced over the contour of the side wall 27 and are separated from each other by arms 34 on the contour of this wall 27.

The side wall 27 also has at its first end 31 three notches 35 regularly spaced over the contour of this end 31.

The front wall 28 is in the form of a circular plate forming a removable cover and this front wall 28 is made of metal.

Three lugs 36 project from the contour of this front wall 28, which are regularly spaced and configured in order to be received inside the notches 35 of the side wall 27; thus allowing correct assembly of the removable cover formed by this front wall 28 with the side wall 27.

This front wall 28 also has a rectangular orifice 37 arranged in its centre.

The back wall 29 is also in the form of a circular plate and this back wall 29 is made of metal.

A connecting element 39 projects centrally from this back wall 29. This connecting element 39 is rectangular in shape and has a hole through its centre.

The drum 6 also has three longitudinal blades 40 each in the form of a plate folded at an angle of approximately 120° C.

These three blades 40 are fixed longitudinally to an internal side surface 38 of the side wall 27 at the respective arms 34.

Each blade 40 has a fold directed towards the inside of the drum 6.

As will be seen in more detail below, these three blades 40 conform to the internal side surface 38 of the side wall 27 in such a manner that the French straws 5 introduced into the drum 6 are set in motion with respect to each other and with respect to the side wall 27 of the unit 6, in other words the French straws 5 are stirred, when the latter is in rotation on itself, with an axis of rotation which is coaxial with the side wall 27.

The drum 6 also has three magnetic components 41 here formed by studs.

These studs 41 are each arranged between a blade 40 and the internal side surface 38 of the side wall 27, close to the first end 31 of this side wall 27.

The front wall 28 forming the removable cover can thus be arranged against the internal side surface 38 of the side wall 27 (in other words inside this side wall 27) and is held by magnetism thanks to the magnetic stud 41.

Opposite, the back wall 29 is permanently fixed to the side wall 27 at its second end 32.

It will be noted that the front wall 28 is mounted close to the first end 31 of the side wall 27 but not flush with this first end 31, unlike the back wall 29 which is mounted flush with the second end of the side wall 27.

The method for freezing the French straws 5 using the freezing system 3 will now be described.

As seen with reference to FIG. 17, a user wishing to implement all of the process for freezing the French straws must select a number, predetermined or not, of French straws 5 and introduce these French straws 5 into the internal space 30 of the drum 6 (Step E1).

The French straws 5 are arranged loose but longitudinally in the longitudinal direction in which the side wall 27 extends.

Of course, the removable cover formed by the front wall 28 of the drum 6 is put in place so as to close the front of the drum 6 so that the French straws 5 cannot escape from the internal space 30 of the drum 6.

It will be noted that the French straws 5 must have a length suited to the length of the drum 6 so that they do not escape through the windows 33.

Then, the drum 6, which is here removable, is introduced into the upper zone 12 of the freezing system 3, the cover 8 been previously opened.

The drum 6 is arranged horizontally facing the support 25 of the rotating shaft 23, with the front wall 28 which has been fixed by magnetism to this support 25 thanks to this front wall which is made of metal and to the magnetic portion 26 comprised by this support 25.

It will be noted that here the drum 6 is mounted coaxially with the rotating shaft 23. The axis of rotation of the drum 6 is therefore also coaxial with the side wall 27 and the drum 6 is thus configured in order to be driven in rotation on itself.

Then, the user can start the unit for driving in rotation 19, i.e. supply the electric motor 21 with electricity in order to rotate the rotating shaft 23 and thus set the drum 6 in rotation on itself.

The setting of the drum 6 in rotation on itself makes it possible, thanks to the three blades 40, to set French straws 5 arranged in this drum 6 in motion in the manner indicated above.

The user can then pass a flow of the cooling agent into the upper zone 12 so that this flow meets the drum 6 and freezes the volumes of biological substance.

The fluid path taken by the gaseous nitrogen is represented by arrows in FIG. 1.

For this, the injection device (not shown) is set in operation in order to inject the liquid nitrogen via the duct 15 into the lower zone 11, in the centre of the turbine 14.

The liquid nitrogen is injected above and in the centre of the turbine 14, at the orifice 16 arranged in the separation plate 13.

The liquid nitrogen is thus supplied to the lower zone 11 which is substantially at atmospheric pressure.

Therefore, the liquid nitrogen is subjected to an expansion phenomenon since it is previously under pressure and this expansion phenomenon causes it to pass from its liquid phase to its gaseous phase so that the blades of the turbine 14 expel the flow of gaseous nitrogen into the upper zone 12, first causing it to pass under the plate 13.

In fact, this flow of gaseous nitrogen first flows under the separation plate 13 then meets rounded walls (not shown) which guide it from the lower zone 11 towards the upper zone 12 so that the flow of gaseous nitrogen rises into the upper zone 12 in the direction of the drum 6 which is in rotation on itself.

The flow of gaseous nitrogen continues on its way until it meets a lower face of the guide plate 17 which is configured so that the flow of gaseous nitrogen is directed directly towards the drum 6.

This flow of gaseous nitrogen thus meets the drum 6 and more particularly, the flow of gaseous nitrogen successively and directly meets the external side surface 42 of the side wall 27 and the French straws 5 since the flow of gaseous nitrogen passes through the windows 33 (and as a result the flow also meets the internal side surface 32).

Here, the flow of gaseous nitrogen meets the drum 6 transversally, i.e. this flow meets the side wall 27 substantially perpendicularly and also enters the internal space 30 via the windows 33 substantially perpendicularly.

This freezing step (or freezing sub-step) is carried out for a predetermined period.

Here, the volumes of biological substance present in the French straws 5 benefit from good heat exchange due to the stirring of these French straws 5, from the conduction phenomenon to which they are subjected via the side wall 27 and from the convection phenomenon to which they are subjected due to the windows 33.

As seen previously, it is possible for the user to repeat this freezing step in other freezing systems at lower and lower temperatures.

Figure 8:
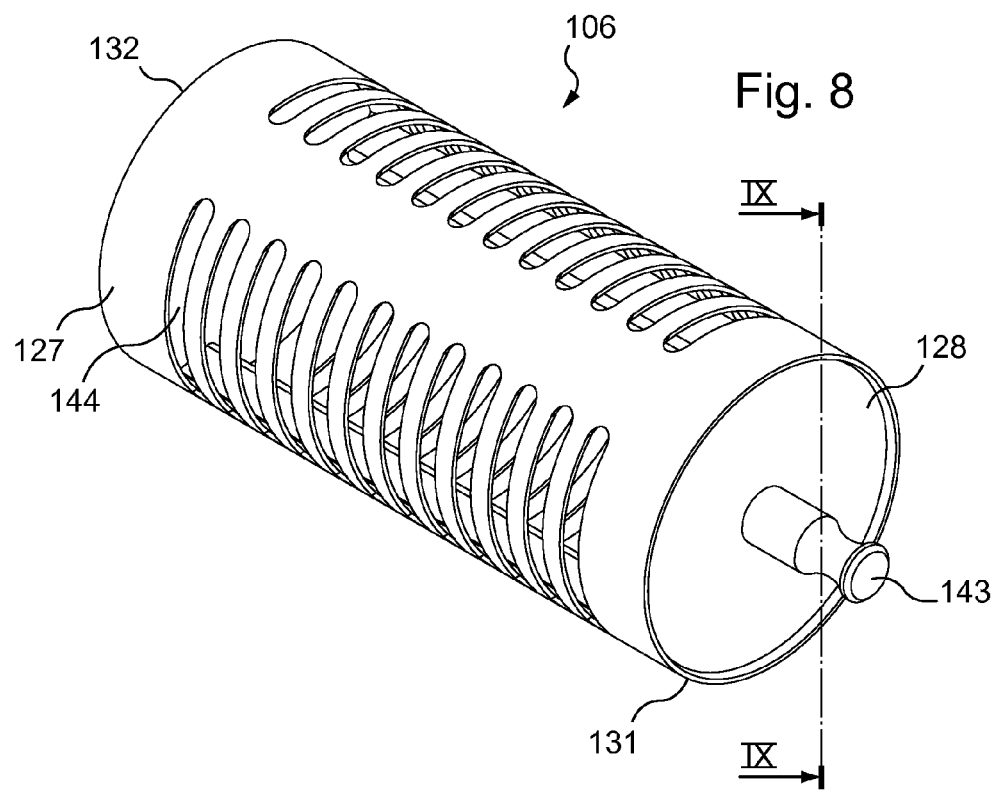
FIGS. 8 to 10 are views similar to those of FIGS. 5 to 7 showing a variant of the conditioning unit.
Figure 9:
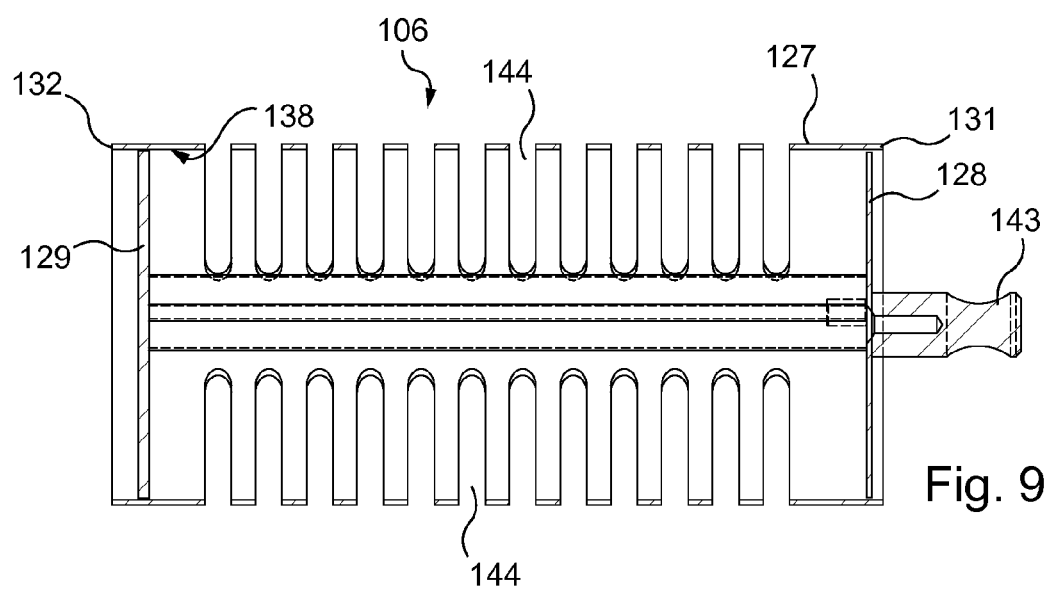
Figure 10:
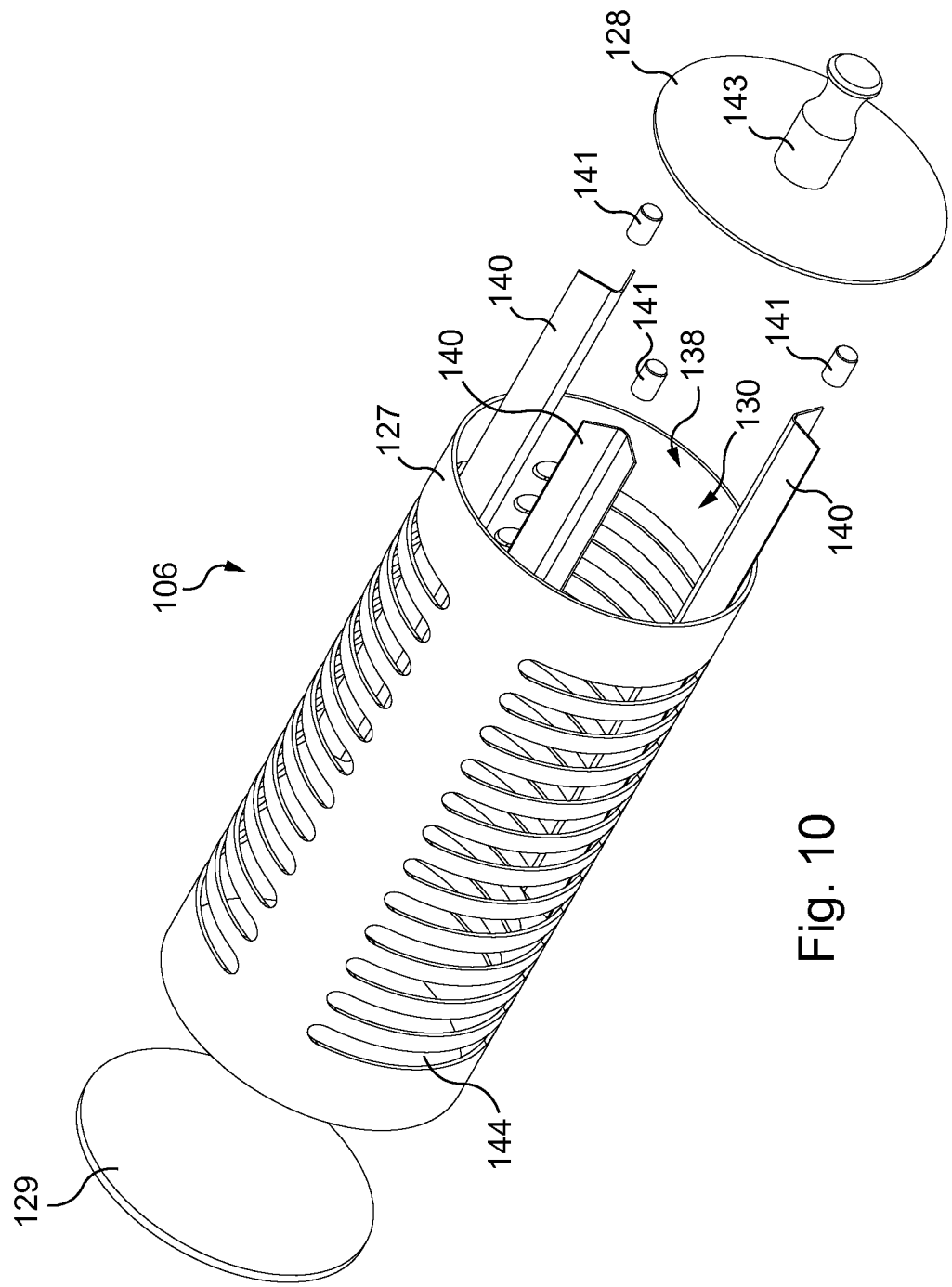

An embodiment variant of the drum will now be described with reference to FIGS. 8 to 10.

Figure 5:
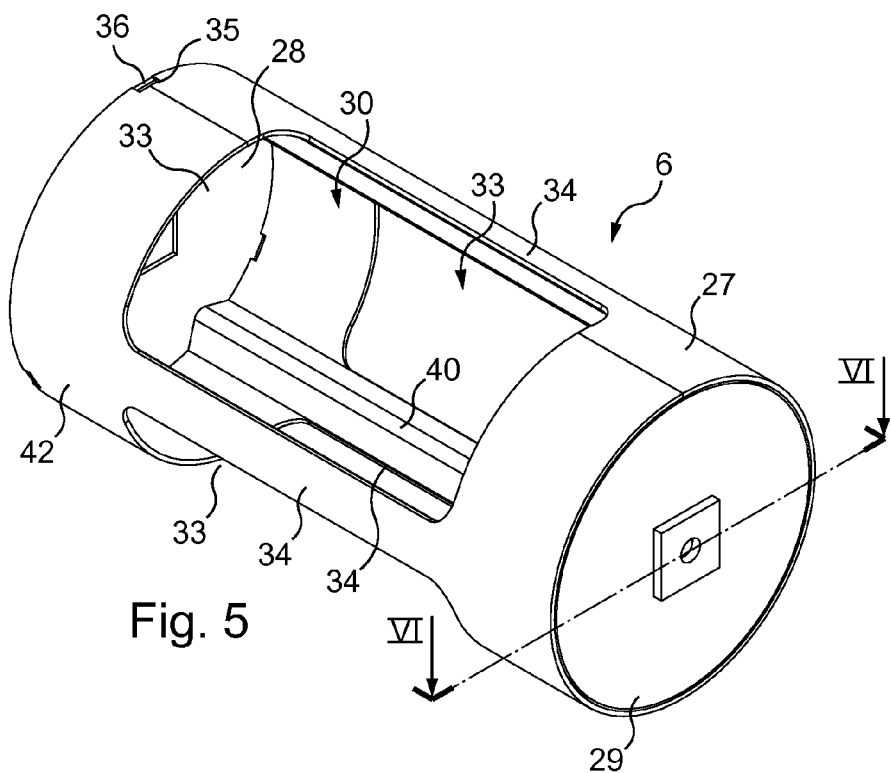
FIG. 5 represents, diagrammatically in perspective and in an isolated manner, the conditioning unit of FIG. 1.
Figure 6:
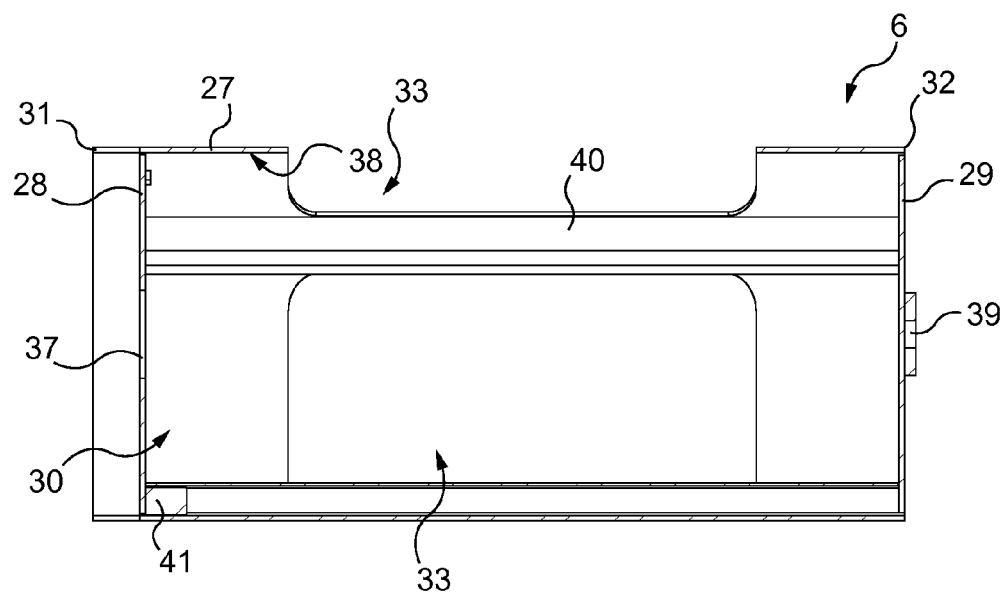
FIG. 6 is a cross-sectional view along VI-VI in FIG. 5.
Figure 7:
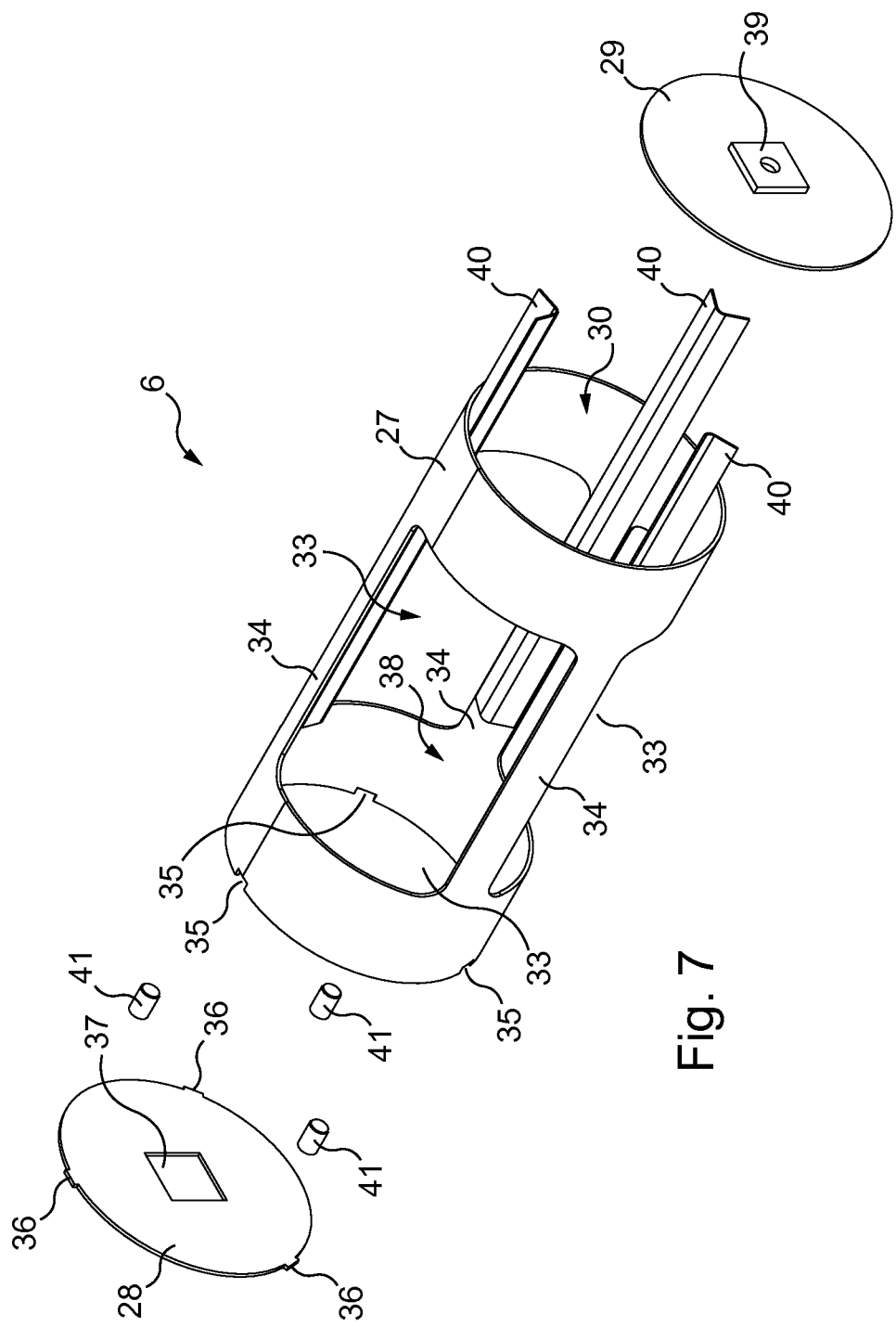
FIG. 7 represents, diagrammatically in perspective and in an exploded manner, the conditioning unit of FIG. 5.

Generally, for similar elements, the same references have been used as for the drum 6 illustrated in FIGS. 5 to 7 but with the number 100 added.

The drum 106, more generally called a conditioning unit, has substantially the same general shape as the drum 6 and has substantially the same characteristics as this drum 6.

In fact, the drum 106 has a general cylindrical shape with an internal space 130 defined by a cylindrical side wall 127, a front wall 128 and a back wall 129.

Moreover, in a manner similar to the drum 6, the drum 106 has three blades 140 arranged against the internal side surface 138 of the side wall 127 as well as three magnetic studs 141 each arranged between a blade 140 and the internal side surface 138.

Unlike the drum 6, the drum 106 has openings formed here by a series of slots 144 which pass through the side wall 127 and which are successively arranged in the longitudinal direction of the drum 106.

Each slot 144 also has a main direction distinct from the longitudinal direction and in particular here, these slots 144 each extend in a direction perpendicular to the longitudinal direction.

Each opening of the drum 106 has twelve identical slots 144 and the drum 106, just like the drum 6, has three openings regularly spaced over the contour of the side wall 127.

Moreover, the side wall 127 of the drum 106 has no grooves at its first end 131.

The drum 106 also has a gripping portion 143 arranged projecting centrally from the front wall 128, in place of the orifice 37 arranged on the front wall 28 of the drum 6.

The back wall 129 is a plate made of solid metal and has no connecting element like the connecting element 39 of the back wall 29 of the drum 6.

Just like the drum 6, the front wall 128 of the drum 106 is removable and mounted by magnetism thanks to the stud 141 and to the fact that this front wall is made of metal; and this front wall 128 is mounted against the internal side surface 138 of the side wall 127, close to the first end 131, but not flush with this first end 131.

Unlike the drum 6, the back wall 129 of the drum 106 is not mounted flush with the second end 132 of the side wall 127 but just like the front wall 128, the back wall 129 is mounted against the internal side surface 138 of the side wall 127, close to this second end 132.

This back wall 129 is permanently fixed to the side wall 127.

FIGS. 11 to 16 illustrate a second embodiment of the freezing system.

Generally, for similar elements the same references have been used as used for the freezing system 3 in FIGS. 1 to 4 but with the number 200 added and the same references have been used as for the drum 6 in FIGS. 5 to 7 but also with the number 200 added.

Figure 11:
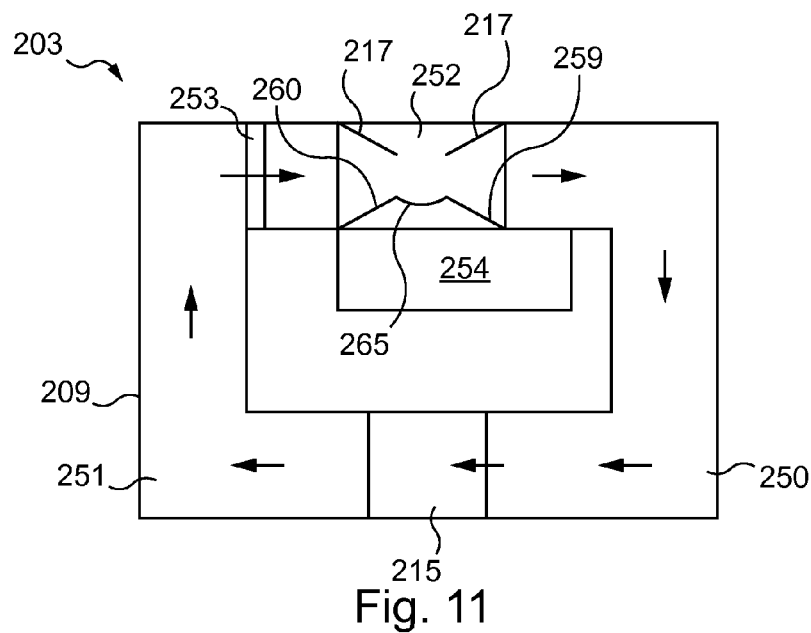
FIG. 11 represents diagrammatically a freezing system according to a second embodiment, which system comprises a freezing zone into which several conditioning units are introduced.
Figure 12:
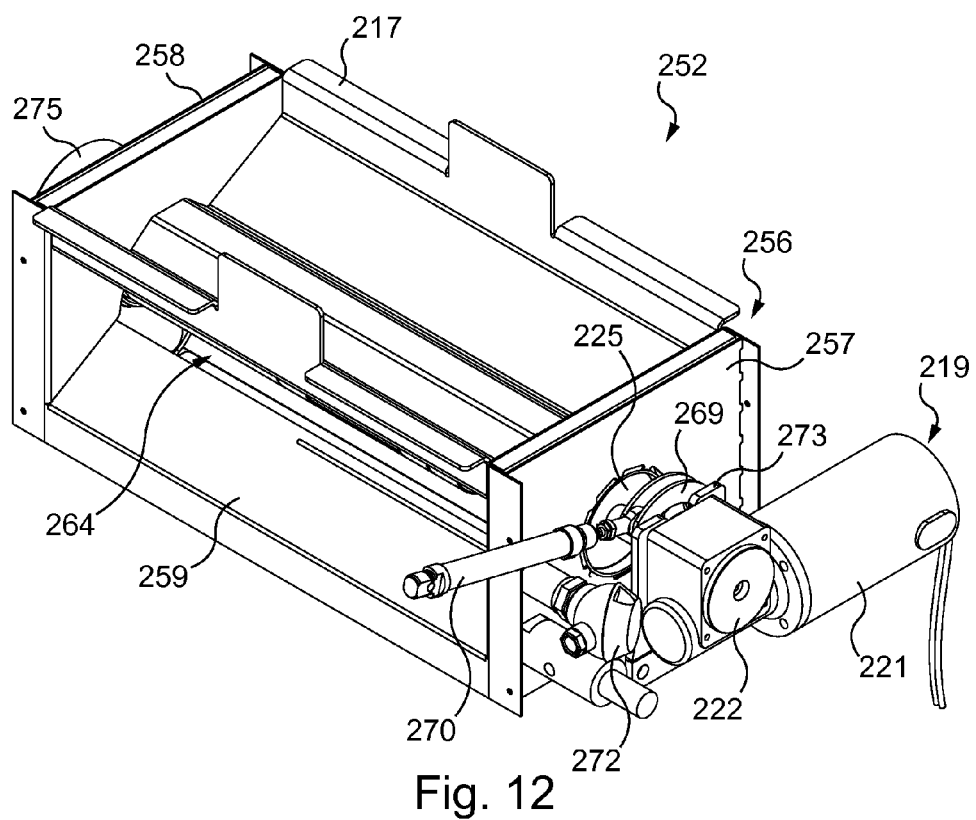
FIG. 12 represents, diagrammatically in perspective and in an isolated manner, the freezing zone visible in FIG. 11.
Figure 13:
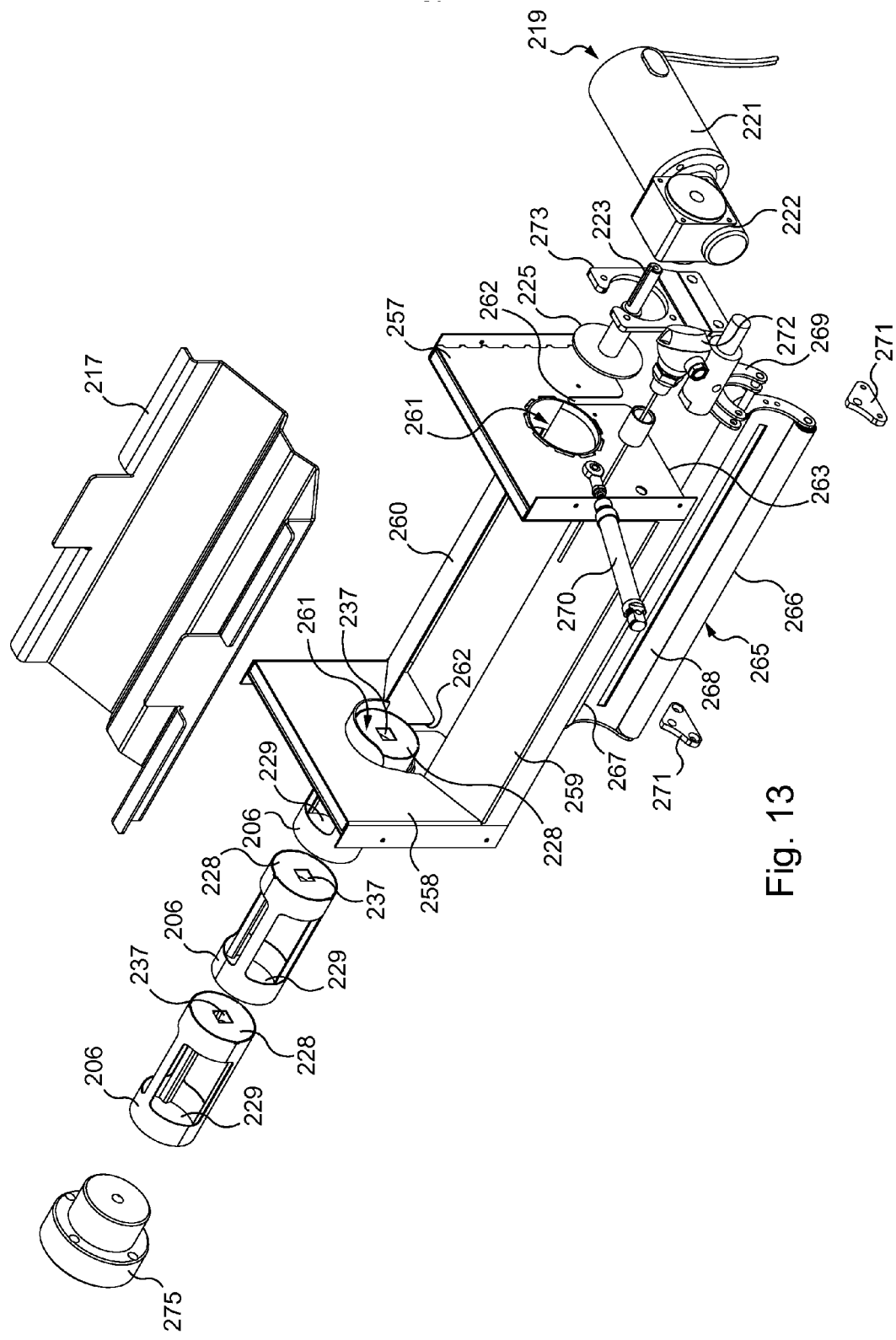
FIG. 13 represents, diagrammatically in perspective and in an exploded manner, the freezing zone of 12.
Figure 14:
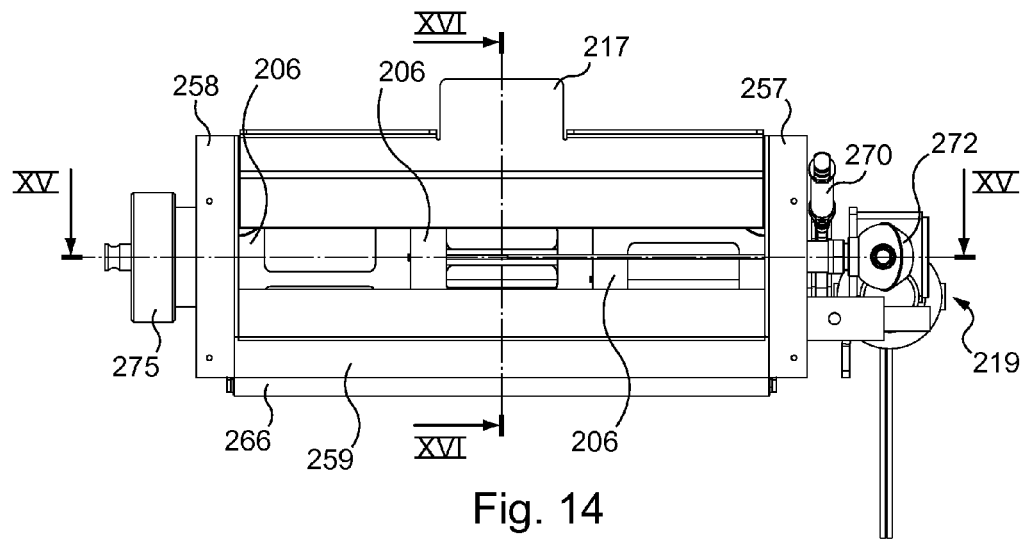
FIG. 14 is a front view of the freezing zone of FIG. 12.
Figure 15:
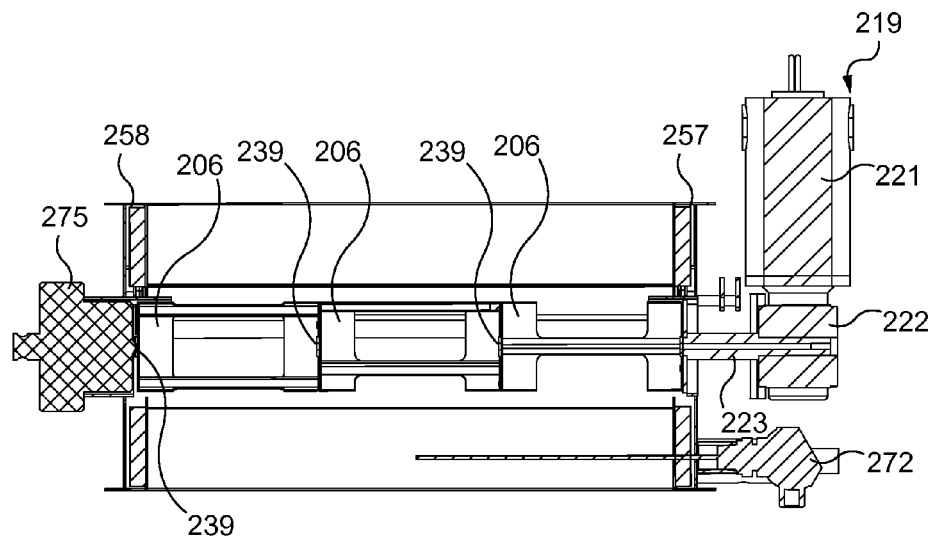
FIGS. 15 and 16 are cross-sectional views along XV-XV and XVI-XVI in FIG. 14.
Figure 16:
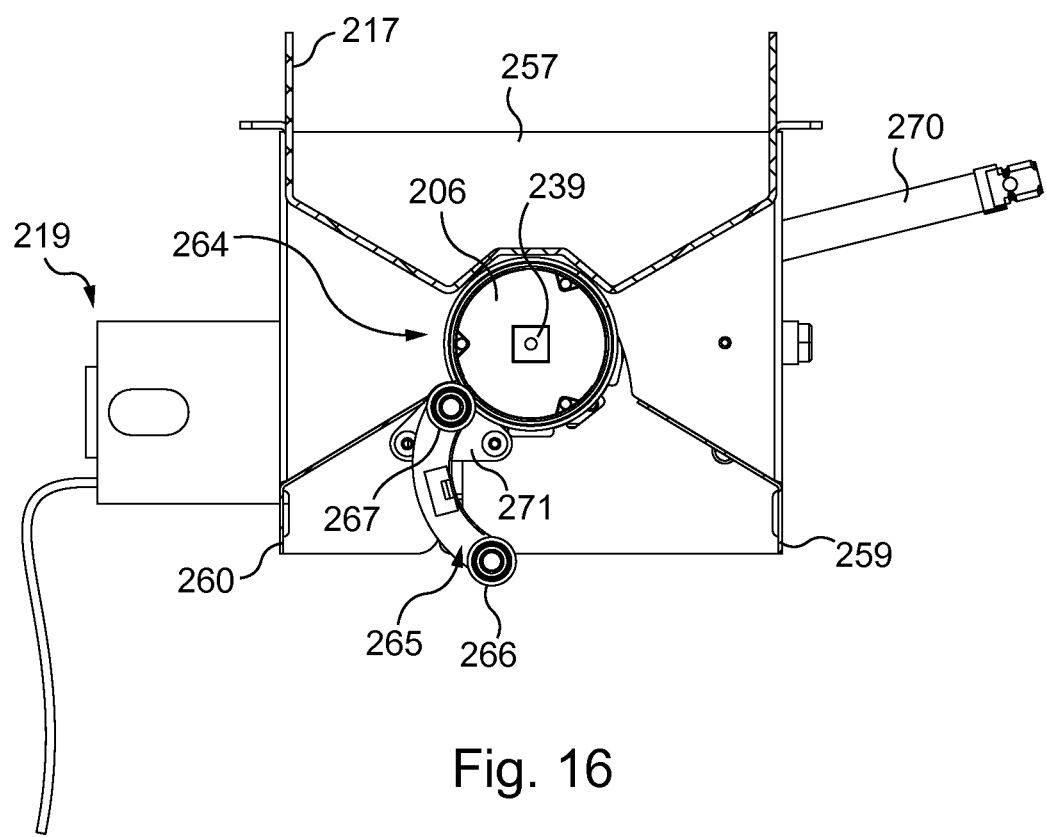

The freezing system 203 is in the form of a gas stream represented very diagrammatically in FIG. 11.

This gas stream 203 comprises a cooling enclosure 209, a centrifugal fan 250 and a part 215 of an injection device for liquid nitrogen originating from an external reservoir (not shown).

The cooling enclosure 209 is formed by a guide channel 251 for the flow of cooling agent (the gaseous nitrogen), a channel 251 into which a flow conditioner 253 is introduced close to a freezing zone 252.

The flow conditioner 253 makes it possible to conveniently direct the gaseous flow and at the same time accelerate it in the direction of the freezing zone 252, thanks to its honeycomb or grid structure.

The freezing system 203 also has a recovery zone 254 arranged under the freezing zone 252.

The fluid path taken by the gaseous nitrogen is represented by arrows in FIG. 11.

The freezing zone 252 is configured in order to receive several drums 206 which can be seen in FIGS. 12 to 16.

The freezing zone 251 has ribs 217, 259 and 260 for guiding the gaseous flow at its inlet and at its outlet as well as a component 265 for holding the drums 206, as will be seen in detail below.

The recovery zone 254 is configured in order to recover these drums 206 once the volumes of biological substance are frozen. This zone 254 is formed by a removable drawer having a plate (not shown) for receiving the drums 206, this plate dividing this zone into two parts, a lower part in which liquid nitrogen is present and another upper part in which gaseous nitrogen is present so as not to create too great a temperature gradient between the freezing, recovery and storage steps.

The freezing system 203 also has a unit for driving in rotation 219 (not visible in FIG. 11) which is mounted on the outside of the freezing zone 252.

A more detailed description of this freezing zone 252 will now be given with reference to FIGS. 12 to 16.

The freezing zone 252 has a metal frame 256 formed by two side plates 257 and 258 which are opposite one another and by two supports 259 and 260 (forming the guide ribs) which are themselves also opposite one another (FIGS. 12 and 16) and which each join the two side plates 257 and 258.

Each side plate has in its centre a circular orifice 261 as well as a slot 262 arranged over a part of the height of each side plate 257, 258 and which opens onto a respective lower edge 263 of each of the side plates 257, 258.

The freezing zone 252 also has a guide plate 217 (also forming a guide rib) for the flow of gaseous nitrogen, which plate 217 is arranged facing the supports 259 and 260, between the side plates 257 and 258 and opposite the lower edges 263 of these side plates 257, 258.

Assembled in this way, the freezing zone 252 has an internal channel 264 intended to receive three drums 206.

It will be noted that these drums 206 are identical to the drum 6 illustrated in FIGS. 5 to 7.

These three drums 206 are arranged in the freezing zone 252 and in particular in the internal channel 264 in an aligned manner in the longitudinal direction.

These drums 206 are fixed in pairs using the orifices 237 that they comprise in their respective front wall 228 and using the connecting elements 239 (FIGS. 15 and 16) that they comprise on their respective back wall 229.

The holding component 265 of the freezing zone 252 is formed by two rollers 266 and 267 mobile in rotation on themselves and supported by an arc-shaped wall 268.

This holding component 265 also has a pivoting part 269 to which is fixed a cylinder 270 configured so as to cause this holding component 265 to pivot.

Thanks to this cylinder 270, the holding component 265 is configured in order to allow two configurations, a support configuration in which the three drums 206 rest on the two rollers 266 and 267 and an unloading configuration in which the drums 206 no longer rest on the rollers 266 and 267 and drop from the zone 252 in order to slide into the recovery zone 254, on its separation plate.

As will be seen below, this support configuration is allowed when the drums 206 are in rotation on themselves.

This holding component 265 is configured in order to be arranged between the two side plates 257 and 258, just below the internal channel 264; and the pivoting part is configured in order to be arranged, with the cylinder 270, on the outside of the side plate 257.

This holding component 265 is fixed to the side plate 257 and to the side plate 258 using fixing brackets 271.

The freezing zone 252 also comprises a temperature probe 272 situated on the outside of the side plate 257 and provided with a rod entering the internal space of the zone 252.

The unit for driving in rotation 219 is similar to the unit for driving in rotation 19 which can be seen in FIGS. 2 to 4.

This unit for driving in rotation 219 is therefore provided with an electric motor 221, a reduction gear 222, a rotating shaft 223 and a support 225 provided with a magnetic portion (not shown).

This unit for driving in rotation 219 is fixed to an interface plate 273 itself fixed to the side plate 257.

One of the drums 206 is configured in order to be fixed by magnetism to the support 225 of the unit for driving in rotation 219, which support 225 is configured in order to be passed through the orifice 261 in the side plate 257.

The freezing zone 252 also has a magnetic stopper 275 situated opposite the support 225 and configured in order to rest against another of the drums 206 (situated opposite the drum 206 fixed to the support 225) for the purpose of holding the three drums 206 aligned and arranged against each other.

The use of the freezing system 203 will now be described.

The steps of filling the French straws with the volumes of biological substance, and partial filling of the drums with the French straws will not be repeated here since the drums 206 are identical to the drum 6 and are partially filled with French straws in the same manner as described above and in the same proportions.

Unlike the method described above, three drums 206 are here inserted into the freezing zone 252 in a longitudinally aligned manner.

For this, the three drums are placed against each other, i.e. with the connecting element 239 projecting from the back wall 229 of a first drum 206 which is received in the orifice 237 in the front wall 228 of a second drum and with the connecting element 239 projecting from the back wall 229 of this second drum 206 which is received in the orifice 237 in the front wall 228 of a third drum 206.

The three drums 206 are inserted into the internal channel 264 of the freezing zone 252 until the first drum 206 meets the support 225 of the unit for driving in rotation 219 where they are then fixed together by magnetism.

The three drums 206 are inserted into the freezing zone 252 through the orifice 261 in the side plate 258 and the magnetic stopper 275 is in turn partially inserted through this orifice 262 until it comes into contact with the back wall of the third drum 206 so that these three drums 206 are tightly interposed between this stopper 275 and the support 225.

At this point in time, the holding component 265 is in its support configuration and the three drums 206 rest on the two rollers 266 and 267.

Then, the unit for driving in rotation 219 is set in operation so that the three drums 206 are driven in rotation on themselves, their respective axis of rotation being coaxial with their respective side wall.

The drums 206 turn on themselves and, as they are supported by the mobile rollers 266 and 267, the latter also turn on themselves.

Finally, the nitrogen arrives via the part 215 of the injection device, expands to become gaseous, moves into the channel 251, passes through the flow conditioner 253 then moves towards the freezing zone 252 until it is guided by the ribs formed by the guide plate 217 and the support 260 of this zone 252 and thus sent directly to the level of the internal channel 264 of this zone 252 where the drums 206 which contain French straws are arranged in rotation on themselves.

As the drums 206 are similar to the drum 6, the French straws which are introduced into them are set in motion with respect to each other and with respect to the side wall 27 of the unit 6, in other words the French straws are stirred, and benefit from very good heat exchange, being subjected to both the convection phenomenon thanks to the windows arranged in these drums 206, and to the conduction phenomenon thanks to the side walls of these drums 206.

The flow of gaseous nitrogen then leaves the freezing zone 252 in order to reach the centrifugal fan 250 and then again be sent into the channel 251.

Once the French straws in the drums are frozen, the cylinder 270 is activated so that it acts on the pivoting part 269 in order to cause the holding component 265, in particular the arc-shaped wall 268, to pivot and thus lower the roller 266.

In this way, the drums 206 are no longer supported by the two rollers 266, 267 and these drums 206 drop from the freezing zone 252 and land on the separation plate of the recovery zone 254 which is in the form of a removable drawer.

The drums 206 are recovered from this drawer 254, where they are found in gaseous nitrogen, before these French straws are placed in storage where they are immersed in liquid nitrogen.

In variants not illustrated:
- the flow of gaseous nitrogen is not perpendicular to the side wall of the drum as is the case in FIGS. 1 to 17, rather the flow is slightly inclined; this can be due to the fact that the axis of rotation of the drums is not coaxial with the side wall and, as a result, the trajectory described by the drums is rather conical;
- the axis of rotation of the drums is not coaxial but rather eccentric;
- the openings differ from windows or slots, rather, these openings are in a grid form or are formed by a succession of holes arranged in the side wall, these holes being identical in shape or having different shapes;
- the drums comprise a greater or lesser number of slots and/or windows than illustrated in the figures;
- the conditioning unit contains a greater or lesser number of French straws, whilst its capacity remains greater than the plurality of French straws;
- the conditioning unit has no opening arranged on the longitudinal side wall;
- the conditioning unit formed by the drum is not fixed to the rotating shaft by magnetism but is, rather, mounted in a self-tightening manner or via a clip or via a clamp;
- the conditioning unit formed by the drum comprises a side cover arranged on the longitudinal side wall rather than a cover formed by the front wall of this drum;
- the raised sections of the conditioning unit are not formed by blades, but rather by rods or by protuberances having other shapes, or there is no raised section;
- the conditioning unit has shapes other than a circular, or even cylindrical shape, for example the conditioning unit has a rectangular or more generally polygonal, or even elliptical cross-section;
- the temperature kinetics is different as the filling of the French straws is carried out directly at a temperature of the order of approximately 4° C. and therefore the equilibration step is not necessary, the French straws are directly arranged in a freezing system;

the box 7 is not provided with a cover having a glazed opening making it possible to see inside the chamber 9;

the filling of the French straws takes place at a temperature of the order of approximately +4° C. and therefore no equilibration step is necessary, the French straws are thus directly introduced loose into the drum, which is introduced into the freezing system;

the freezing systems do not benefit from forced-type convection but rather from natural convection; and/or the unit for driving in rotation is not fixed to the cooling enclosure in which the flow of cooling agent circulates, but the freezing system is in the form of a tunnel having a succession of zones at different temperatures with a conveyor for causing the conditioning unit to pass successively into the different zones (of course, a separating element such as a small curtain, for example made of Kevlar, is provided between the different zones and this element withdraws when the conditioning unit passes); and the conveyor for example has locations on the rotating rollers on which the conditioning unit is held in order to be set in rotation on itself.

It is more generally recalled that the invention is not limited to the examples described and represented.

The invention claimed is:

1. An assembly for freezing a plurality of conditioning tubes, each conditioning tube in the plurality of conditioning tubes being filled with a predetermined volume of biological substance, in which each said conditioning tube is driven in rotation in a flow of cooling agent, said assembly comprising
a cooling enclosure configured to be passed through by said flow of cooling agent, and
a conditioning unit which is removable and placed in said cooling enclosure, said conditioning unit being provided with a greater capacity than said plurality of said conditioning tubes to directly receive said plurality of said conditioning tubes, and said cooling enclosure being fixed;
a unit for driving said conditioning unit in rotation, said unit for driving in rotation being provided with a connection interface on which said removable conditioning unit is placed; and
a receptacle defined by the conditioning unit, the receptacle having a central longitudinal axis, an outermost longitudinal side wall exposed to an external environment of the conditioning unit, a plurality of blades disposed on an internal side surface of the longitudinal side wall, at least one opening to the external environment defined in the outermost longitudinal side wall, and an internal space defining the capacity of the conditioning unit, said internal space being configured to receive the plurality of conditioning tubes in the longitudinal direction of said at least one longitudinal side wall, such that said plurality of conditioning tubes do not completely fill the conditioning unit;
wherein the unit for driving the conditioning unit is axially connected to said conditioning unit to drive the receptacle in rotation such that the conditioning unit spins and the plurality of conditioning tubes are stirred in the internal space of the conditioning unit and in the flow of cooling agent due to the plurality of blades and the at least one opening;
wherein the assembly comprises the plurality of conditioning tubes each filled with a predetermined volume of biological substance;
wherein the connection interface is located between the unit for driving in rotation and the conditioning unit and that the conditioning unit is removably placed on said connection interface; and
wherein the flow of cooling agent is a gaseous fluid that passes through the enclosure.

2. The assembly according to claim 1, further comprising an equilibration system operable at a first predetermined stable temperature and configured to receive said at least one conditioning unit during a first predetermined period.

3. The assembly according to claim 1, further comprising at least one freezing system provided with at least one freezing zone formed by said cooling enclosure, said at least one freezing zone being configured to be cooled down by said flow of cooling agent which circulates in said cooling enclosure between a second predetermined temperature and a third predetermined temperature.

4. The assembly according to claim 3, wherein said second predetermined temperature is below or equal to said third predetermined temperature.

5. The assembly according to claim 1, wherein said unit for driving in rotation is mounted on said cooling enclosure.

6. The assembly according to claim 5, wherein said unit for driving in rotation is fixed to the outside of said cooling enclosure and has a drive shaft extending from said unit for driving in rotation and continuing until said drive shaft opens inside said cooling enclosure, said drive shaft being provided at one end of said connection interface (25; 26; 225), said one end being situated in said cooling enclosure.

7. The assembly according to claim 6, wherein said connection interface is formed by a support provided with a fixing part configured to cooperate with said conditioning unit.

8. The assembly according to claim 7, wherein said conditioning unit has a metallic back wall and the fixing part is formed by a magnetic portion arranged in said support, said magnetic portion allowing the fixing of said conditioning unit to said support by magnetism, using said back wall.

9. The assembly according to claim 1, wherein said conditioning unit is configured to be placed in said cooling enclosure so that said flow of cooling agent meets said side wall.

10. The assembly according to claim 1, wherein said at least one conditioning unit is arranged in said enclosure so that said flow of cooling agent passes through said opening in order to meet said conditioning tubes (5).

11. The assembly according to claim 10, wherein said at least one opening is in the form of a window extending in said longitudinal direction.

12. The assembly according to claim 11, wherein said at least one opening is formed by a series of through slots arranged successively in said longitudinal direction, each slot having a main direction distinct from said longitudinal direction.

13. The assembly according to claim 1, wherein said conditioning unit further comprises a metallic removable cover and at least one magnetic component allowing said removable cover to be fixed to said side wall by magnetism.

14. The assembly according to claim 13, wherein said cover has a gripping portion.

15. The assembly according to claim 1, further comprising several conditioning units each provided with a front wall and a back wall opposite said front wall, which, with said side wall, at least partially define said internal space; a first of said conditioning units has a receiving orifice arranged in said front wall and configured to receive a connecting element projecting from a back wall of a second of said conditioning units with which said first conditioning unit is arranged to cooperate; and said first conditioning unit has a connecting element projecting from said back wall and configured to be introduced into a receiving orifice arranged in a front wall of a third of said conditioning units with which said first conditioning unit is also arranged to cooperate.

16. The assembly according to claim 1, wherein said conditioning unit has a front wall and a back wall opposite said front wall which, with said side wall, at least partially define said internal space; said front wall is configured to be mounted flush with a first end of said side wall; and said back wall is configured to be mounted against said internal side surface of said side wall, close to a second end of said side wall which is opposite said first end.

* * * * *